(12) United States Patent
Rustenburg et al.

(10) Patent No.: US 6,423,732 B1
(45) Date of Patent: Jul. 23, 2002

(54) SYNERGISTIC COMBINATIONS OF CYPROCONAZOLE

(75) Inventors: Gerbrand Rustenburg, Heemstede; Cor J. Klaver, Bussum, both of (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 08/468,010

(22) Filed: Jun. 6, 1995

Related U.S. Application Data

(63) Continuation of application No. 08/011,688, filed on Feb. 2, 1993, now abandoned.

(30) Foreign Application Priority Data

Feb. 4, 1992 (DE) .......................................... 42 03 090

(51) Int. Cl.⁷ ........................ A01N 43/653; A01N 33/12
(52) U.S. Cl. ........................ 514/383; 514/642; 514/643
(58) Field of Search ................................. 514/383, 642, 514/643

(56) References Cited

U.S. PATENT DOCUMENTS

| | | | | |
|---|---|---|---|---|
| 4,664,696 A | * | 5/1987 | Schaub ........................ 514/184 |
| 4,888,049 A | * | 12/1989 | Iwasaki et al. ............. 514/786 |
| 5,874,456 A | * | 2/1999 | McDade ..................... 514/383 |
| 5,972,971 A | * | 10/1999 | Hever et al. ................ 514/341 |

FOREIGN PATENT DOCUMENTS

| EP | 0237764 | * | 9/1987 |
| EP | 1025967 | * | 8/2000 |

* cited by examiner

*Primary Examiner*—John Pak
(74) *Attorney, Agent, or Firm*—William A. Teoli, Jr.

(57) ABSTRACT

The invention relates to novel fungicidal compositions based on cyproconazole and quaternary ammonium salts which have surprisingly powerful synergistic effects in the control and prevention of wood-destroying fungi.

12 Claims, No Drawings

SYNERGISTIC COMBINATIONS OF CYPROCONAZOLE

This application is a continuation of application Ser. No. 08/011,688, filed Feb. 2, 1993 now abandoned.

The cyproconazole-type fungicides found in recent years have good fungicidal activity (cf. U.S. Pat. No. 4,849,439) and have an activity against human and animal dermatophytes and against phytopathogenic fungi.

Novel fungicidal agents based on cyproconazole and quaternary ammonium salts which have surprisingly powerful synergistic activities in the control and prevention of wood-destroying fungi have now been found.

The use of mixtures which entail synergistic effects has considerable economic but also ecological advantages.

Synergism is to be understood as meaning the mutually enhancing activity of two or more substances. In the present case, the combined application of two fungicides allows the application rate of the fungicides to be reduced while still maintaining an equally good fungicidal activity, or that identical application rates of the fungicides result in a greater activity than the activity to be expected from the individually employed active substances.

The utilization of such synergistic effects allow the application rates of the components to be considerably reduced, and it is possible to control a broad range of wood-destroying fungi. The reduced application rates relate to the quaternary ammonium salts, but also to cyproconazole.

In the present case, cyproconazole is combined with compounds which considerably enhance the activity of the fungicide, which allows the identical activity to be obtained by using a lower concentration of the fungicide. In addition, the combinations according to the invention are active even when used at low application rates. They are therefore outstandingly suitable for controlling wood fungi in wood and masonry.

The present invention therefore relates to fungicidal compositions which comprise A) cyproconazole (Formula I)

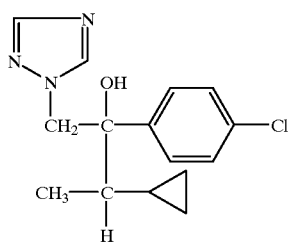

in combination with

B) inorganic or organic ammonium salts of the formula II

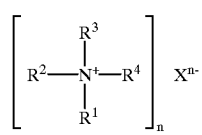

in which $R^1$–$R^4$ are identical or different and are an organic substituent which has up to 18 carbon atoms and which is bonded by a carbon-nitrogen bond, or three of the radicals $R^1$–$R^4$ together with the nitrogen atom form a heteroaromatic system, for example pyridinium, $x^{n-}$ is the anion of an inorganic or organic n-basic acid, and n is 1, 2 or 3.

The compounds of type B are preferably ammonium salts in which $R^1$–$R^4$ are identical or different and are ($C_1$–$C_{18}$)-alkyl, ($C_7$–$C_{13}$)-aralkyl, such as benzyl, ($C_1$–$C_6$)-alkyoxy-($C_1$–$C_{12}$)-alkyl, [—$CH_2$—$CH_2$—O]$_x$—H or [—$CH(CH_3)$—$CH_2$—O]$_x$—H and x is 1, 2 or 3. Particularly preferred salts are those in which $R^1$ and $R^2$ are in each case ($C_1$–$C_4$)-alkyl, in particular methyl, $R^3$ and $R^4$ are in each case ($C_8$–$C_{12}$)-alkyl, in particular decyl. Preferred anions $X^{n-}$ are Cl$^-$, Br$^-$, $SO_4^{2-}$, $HSO_4^-$, $PO_4^{3-}$, $HPO_4^{2-}$, $H_2PO_4^-$, $CH_3COO^-$, $COO_2^{2-}$, $SCN^-$, in particular Cl$^-$.

Most of the wood-destroying fungi are Basidiomycetes, but Ascomycetes and Deuteromycetes can also be found. The compositions according to the invention are preferably used against Basidiomycetes, for example against Coniophora, Gloephyllum, Poria, Serpula and Coriolus. The following fields of application are of particular interest: preventive and curative treatment of wood, and curative treatment of wood and masonry.

The compounds of type B can be combined with cyproconazole to give a range of combinations. Cyproconazole and quaternary ammonium salts are commercially available.

The mixing ratios of the individual components in the combinations according to the invention can vary within wide limits. However, quantitative ratios of between 2:5 and 1:25, preferably between 1:4 and 1:6, are selected for practical reasons.

The mixtures according to the invention can be in the form of water-dilutable concentrations which are then applied in a customary manner in the form of a dilution with water, or in the form of so-called tank mixes which are prepared by concomitant dilution of the separately formulated components with water immediately prior to application. They can also be applied in the form of aqueous ready-for-use solutions.

The application rates of the fungicides of type A in the active substance mixtures are generally between 1 g/l and 100 g/l, the application rates of B are between 5 g/l and 500 g/l; the total amount of product combination to be applied is 15 l/m$^3$ to 600 l/m$^3$ of wood.

The compositions according to the invention can be marketed in the form of the conventional preparations which are known to a person skilled in the art. They are preferably marketed in the form of water-dilutable concentrates or ready-for-use solutions. The formulated compositions contain for example 0.1 to 50% by weight of the active substance combinations according to the invention.

Examples of inert substances which can be used are n-butyl glycolate, polyglycol ether or dipropylene glycol monoethyl ether.

In the case of fungicidal compositions, the concentrations of the active substances in the commercially available formulations can vary. The active substance concentration in emulsifiable concentrates is approx. 1 to 50%.

If appropriate, the commercial concentrates are diluted in the customary manner for application. The application rate and the concentration required varies depending on the field of application, for example for the treatment of wood without or with contact with the soil or water.

A combination of the active substances means that the fungicidal active substances are applied jointly or a few days one after the other, in the form of a so-called split application.

If required, the compositions according to the invention can be combined with other active substances, preferably with fungicides and insecticides. Unless otherwise indicated, percentages are percent by weight. The invention is illustrated by the example which follows without limiting it thereto:

EXAMPLE

Determination of the Activity of the Cyproconazole in Combination with Dimethyldidecylammonium Chloride Against Wood-destroying Basidiomycetes The active substances were tested in accordance with European Testing Standards ES 84 (1979) and 113 (1986). Treatment with the active substances prevents the wood from being destroyed. The effect of the treatment is quantified indirectly via the non-existing weight loss of the wood samples.

The wood sample used was pine sapwood, and the test fungi used were Coniophora puteana (cellar fungus), Poria plazenta, Gloeophyllum trabeum and Trametes (Coriolus) versicolor. Markedly smaller amounts of the combination according to the invention of cyproconazole (A: 2-(4-chlorophenyl)-3-cyclopropyl-3-methyl-1-(1H,1,2,4-triazol-1-yl)-butan-2-ol) and dimethyldidecylammonium chloride (B1) have the same result (0% weight loss) as cyproconazole or B1 alone. Comparably good results were also obtained when beech was used as the wood sample.

TABLE

| | Pine sapwood | | |
|---|---|---|---|
| | Amount (g/m³) of active Substance at 0% | | Weight Loss |
| Fungi | A + B1 | A | B1 |
| Coniophora | 121 g + 605 g | 247 g | 12,415 g |
| Gloephyllum | 119.5 g + 597.5 g | 247 g | 12,505 g |
| Poria | 121 g + 605 g | 243 g | 3,175 g |
| Coriolus | 105 g + 525 g | 418 g | 2,675 g |

What is claimed is:

1. A fungicidal composition which comprises
A) cyproconazole of the Formula I

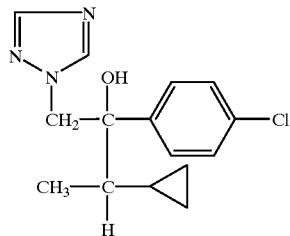

(I)

in combination with
B) inorganic or organic ammonium salts of the formula II

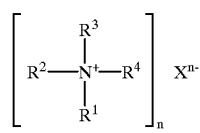

(II)

in which $R^1$–$R^4$ are identical or different and are an organic substituent which has up to 18 carbon atoms and which is bonded by a carbon-nitrogen bond, or three of the radicals $R^1$–$R^4$ together with the nitrogen atom form a heteroaromatic system, $X^{n-}$ is the anion of an inorganic or organic n-basic acid, and n is 1, 2 or 3.

2. A fungicidal composition as claimed in claim 1, which comprises the active substances A and B in a ratio by weight of 1:2.5 to 1:25.

3. The fungicidal composition as claimed in claim 2, wherein the ratio by weight of A:B is 1:4 to 1:6.

4. The fungicidal composition as claimed in claim 1, which comprises 0.1 to 50% by weight of active substance mixture and 99.5–50% by weight of conventional formulation auxiliaries for preparations as sprayable solutions.

5. A method of controlling harmful fungal growth on wood, which comprises applying an effective fungicidal amount of the fungicidal composition according to claim 1 to the wood to be treated.

6. The method as claimed in claim 5 wherein the active substances of the formulae I and II of the fungicidal composition are applied in a ratio by weight of 1:2.5 to 1:25.

7. The method as claimed in claim 6, wherein the active substances of the formulae I and II of the fungicidal composition are applied in a ratio by weight of 1:4 to 1:6.

8. The method as claimed in claim 6, which comprises applying the fungicidal composition in amounts from 15 to 600 l/m³ of wood.

9. The method as claimed in claim 6, which comprises using spray mixtures which comprise 1 to 100 g/l of the compound of the formula I and 5 to 500 g/l of a compound of the formula II.

10. The fungicidal composition according to claim 1 wherein compound B comprises dimethyldidecylammonium chloride and the weight ratio of A:B is 1:4 to 1:6.

11. A fungicidal composition which comprises
A) cyproconazole of the Formula I

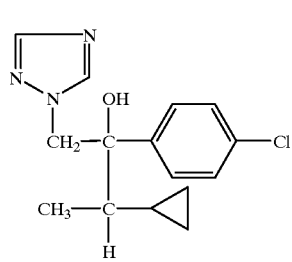

(I)

in combination with
B) inorganic or organic ammonium salts of the formula II

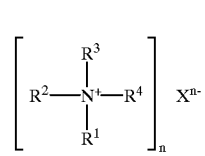

(II)

in which $R^1$ and $R^2$ are each ($C_1$–$C_4$) alkyl and $R^3$ and $R^4$ are each ($C_8$–$C_{12}$) alkyl, $X^{n-}$ is the anion of an inorganic or organic n-basic acid, and n is 1, 2 or 3.

12. The fungicidal composition according to claim 11 wherein $R^1$ and $R^2$ are each methyl and $R^3$ and $R^4$ are each decyl.

* * * * *